United States Patent [19]  
Malley et al.

[11] 4,137,494  
[45] Jan. 30, 1979

[54] APPARATUS AND METHOD FOR ANALYZING OIL CONTENT OF WATER

[75] Inventors: Frank Malley, Gloucester; Raymond F. Akers, Mantua, both of N.J.

[73] Assignee: Delray Electronics Inc., Westville, N.J.

[21] Appl. No.: 772,071

[22] Filed: Feb. 25, 1977

[51] Int. Cl.² ............................................. G01N 27/12
[52] U.S. Cl. ................................ 324/30 R; 204/1 T; 204/195 R; 324/65 R; 324/71 R
[58] Field of Search ................... 324/71 R, 29, 30 R, 324/65 R; 204/1 T, 195 R; 260/2.5 AD

[56] References Cited  
U.S. PATENT DOCUMENTS

| 2,752,586 | 6/1956 | Jordan | 340/235 |
| 3,791,792 | 2/1974 | Lindsay | 23/230 R |
| 3,792,347 | 2/1974 | Hawley | 324/30 R |

FOREIGN PATENT DOCUMENTS 924081 4/1963 United Kingdom .............. 260/2.5 AD

Primary Examiner—G. L. Kaplan  
Attorney, Agent, or Firm—Woodcock, Washburn, Kurtz & Mackiewicz

[57] ABSTRACT

There is disclosed an oil content analyzer device containing a degradable ion transport cell designed to present a changing internal impedance as a function of the oil content of water flowing therethrough. The cell is comprised of two electrodes made of dissimilar metallic compositions with a hydrocarbon-absorbing material sandwiched therebetween, and housed in a container having openings to permit water flow therethrough. In operation, a sample of water is circulated through the degradable ion transport generating device with the result that the electrical output characteristics of the device change as a function of the amount of hydrocarbons absorbed in the membrane element, whereby an electrical signal is generated which is inversely proportional to the oil content of the analyzed water sample.

14 Claims, 3 Drawing Figures

APPARATUS AND METHOD FOR ANALYZING OIL CONTENT OF WATER

BACKGROUND OF THE INVENTION

A. Field of the Invention

This invention lies in the area of oil content analyzing apparatus and methods, and, more particularly, in the area of means and methods for detecting trace amounts of oil in the water being tested.

B. Description of the Prior Art

The need to detect small, or trace amounts of oil in water is a need which has long been present in a variety of commercial and other areas. However, the relatively recent emphasis on protecting and maintaining the marine environment has underscored the need for development of accurate and reliable instrumentation for the detection and measurement of trace amounts of oil in water. The instrumentation presently available, which utilizes present state of the art techniques and devices, is simply not adequate for widespread reliable and commercially feasible utilization. The present instrumentation lies generally in two categories. The first category of device employs the Noll method which uses a gravimetric procedure, i.e., weighing of a sample, and requires that the water sample be taken to a laboratory to determine the oil, or hydrocarbon content of the sample being analyzed. The second type uses the sophisticated technique of spectrophotometry, whereby the presence of hydrocarbons is detected by their absorption of energies in their characteristic ultraviolet and infrared areas of the spectrum. It is understood that attempts have been made to package these devices for on-site analysis, e.g., on boats, but this results in large and expensive instrument packages. Detection of oil in water by these methods and systems requires expensive instrumentation costing literally thousands of dollars, which necessarily limits their use to a relatively small segment of the industrial market. The net effect of the inadequacy of the presently available devices is that many users simply don't have the instrumentation that they desire and, in many cases, need in order to comply with legal regulations. As an example, recreational boat owners, who number in the millions, are required to limit the oil content of discharged bilge water to a limit as low as 15 parts per million of oil. Clearly, for this portion of the large segment of prospective users of oil detection equipment, there is a very great need for a relatively inexpensive and reliable oil detection device having the required sensitivity.

SUMMARY OF THE INVENTION

It is an object of this invention to provide a reliable oil detection device which is sufficiently sensitive to detect trace amounts of oil in water, e.g., 15 ppm and less.

It is another object of this invention to provide a rugged and inexpensive oil detection device which can reliably measure low amounts of oil contained in water.

It is a further object of this invention to provide a solid state oil detection device which can reliably measure trace amounts of oil in water.

It is a further object of this invention to provide a rugged oil detection device which provides output characteristics which vary in a predetermined manner as a function of the oil content of a water sample flowed therethrough, whereby the oil content can be determined by electronic analysis of the output of the oil detector.

It is a further object of this invention to provide a small and rugged detection device which is adapted to detect trace amounts of organic molecules in water, and which is adapted to operate efficiently and reliably at the situs of the water which is to be tested.

It is a further object of this invention to provide an efficient and reliable method of detecting trace amounts of oil or other organic compounds in water at the location of such water.

In accordance with the above objectives, there is provided an oil content analyzer device containing an ionic transport cell having a degradable ion transport member therein designed to present an electrical characteristic which is a function of the oil content of the aqueous solution which is flowed therethrough. In the preferred form, the device contains two electrodes made of dissimilar metals with the degradable ion transport membrane sandwiched therebetween, the electrodes and membrane being housed in a housing having openings designed to permit water flow therethrough. Output terminals are provided on the outside of the container, which are connected to respective electrodes, to provide an output signal. The degradable ion transport device is combined in a system including a water flow subsystem which may have a container for holding a sample of the water to be tested and means for flowing the water from said sample container through the device, whereby hydrocarbons from the oil present in the water are absorbed in the membrane, thus changing the electrical output of the device. The output of the device is connected through to electronic circuitry of suitable matching characteristics, for generation of output signals for indication of oil content level.

DESCRIPTION OF THE PREFERRED EMBODIMENTS

Figure 1:
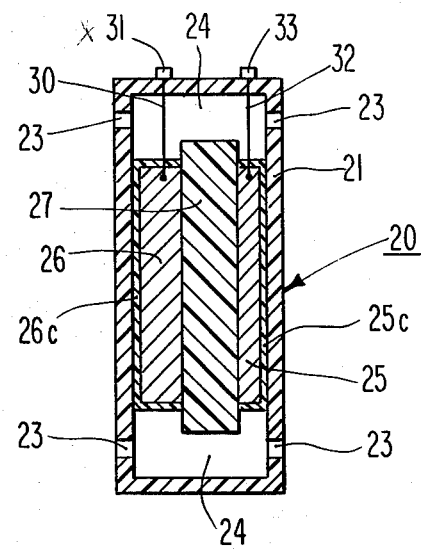
FIG. 1 is a schematic diagram of the degradable ion transport device of this invention.

Referring now to the drawings, and in particular FIG. 1, there is shown a schematic representation of the device of this invention which produces an electrical signal representative of the oil content of a sample of water which has been flowed through such device. The device 20 has a housing 21, suitably made of polyvinylchloride or other like material. Housing 21 contains openings 23 to permit water to flow into and out of the housing, thereby rendering the housing adaptable to having water flow therethrough. It is to be noted that the openings are shown schematically only, and are not meant to be scale representations of the openings for receiving and discharging the water which flows through the device. The exact position and size, as well as number of such openings is a design feature which can be adapted in accordance with the particular application in mind.

Within the housing 21 there is an arrangement comprising electrodes 25 and 26, with a membrane 27 positioned therebetween. Electrodes 25 and 26 are metallic in composition, such compositions being dissimilar. In the preferred embodiment, electrode 25 is zinc, while electrode 26 is sponge copper. Electrodes 25 and 26 each have coatings 25C and 26C respectively as shown. The coating is suitably a porous ABS plastic material, with small holes therethrough. The element 27 is an ion transport membrane, suitably a polyurethane membrane which has the characteristic of passing ions present in the water but absorbing and accumulating hydrocarbons from the oil. The membrane may be natural or artificial sponge, or any hydrocarbon-absorbing material. The requirement of the membrane is that it have a spongy characteristic which enables it to catch organic molecules such as hydrocarbons. The term spongy, as used herein, embraces polyurethane and like plastics.

In practice, electrode 26 is suitably one square inch in area and 0.25 inch thick; electrode 25 is also one square inch in area and about 0.015 inch thick; and element 27 is 0.25 to 0.50 inch thick. Membrane element 27 is preferably sandwiched between electrodes 25 and 26 so that the non-coated surfaces of the electrodes bear against the membrane. The device 20 is suitably cylindrical in overall form. The precise dimensions of the device 20 and of the component elements thereof are a function of the particular design and application, and will generally be varied as a function of the sensitivity of detection required in terms of parts per million of oil in the water.

Figure 2:
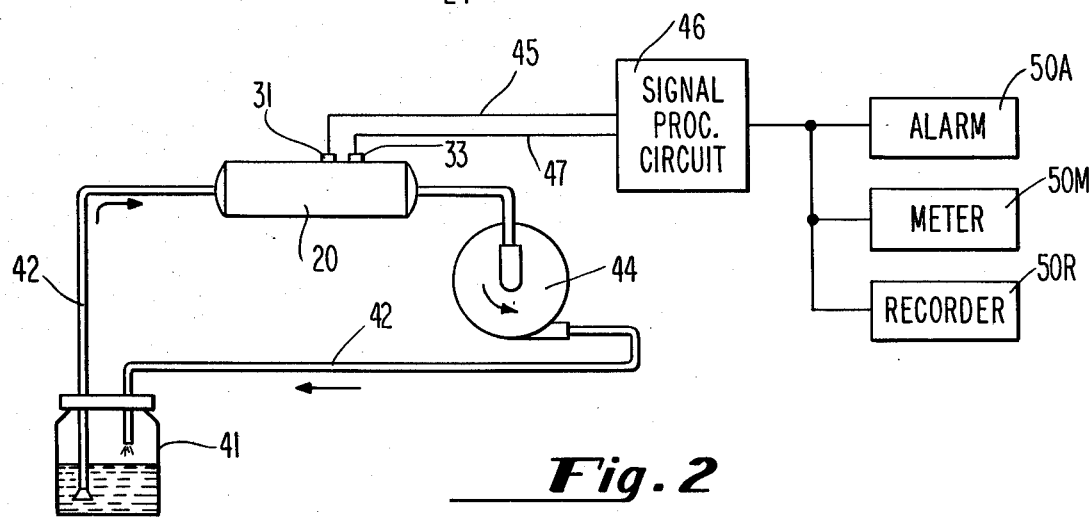
FIG. 2 is a schematic diagram of the system of this invention, illustrating the incorporation of the degradable ion transport device into a water sample flow system, and also showing the means for indicating the oil content.

Referring now to FIG. 2, there is shown a schematic diagram of the system of this invention utilizing the device 20 to measure oil content. The water to be sampled may be sea water, river water, potable drinking water or the like. As used herein, the term water includes aqueous solutions of any form that contain ions in at least small amounts. Water is collected in a sample container shown schematically at 41. The water is drawn through flow means such as piping or tubing 42 under the power of pump 44 through and to the device 20. As shown schematically in FIG. 2, the inlet and outlet openings of device 20 are located in the ends thereof, and the output leads 45 and 47 are taken from terminals 31 and 33 located on the side of the device. The exact point of bringing out the feedthrough lines 30 and 32, which connect the electrodes to terminals 31 and 33, is a matter of design preference. Leads 45 and 47 are connected through to signal processing circuit 46, which suitably includes a DC amplifier. Circuit 46 in turn provides an output to indicators 50A, 50M and/or 50R as shown. A convenient power source, not shown, is utilized for powering the pump 44, the electronic circuitry and indicator elements.

In practice, the sample water is circulated continuously for a predetermined period of time through the device 20 by pump 44. As the water, which contains both ions and oil molecules, is passed through the membrane, the membrane acts as an ion transport medium such that a DC voltage is generated across the terminals 31 and 33 which are connected to the respective electrodes. However, the oil molecules, or hydrocarbons which are in the water, tend to collect in the membrane. Since they are not ions, they do not participate in the ion transport activity. The inorganic compounds which are in the water, such as salt, have ionic structures which dissolve readily in water, and it is these disassociated positive and negative ions which participate in the ion transport activity. The presence of the ions which are diffused through the membrane decreases the impedance of the membrane and makes available at the electrode output a current which is a function of such decreased internal impedance of the detector cell 20. However, when the hydrocarbons are passed through the membrane, they absorb within it and accumulate, thereby reducing the number of charge carrying ions which are present within the fixed volume of the membrane. The replacement of ions by dielectric molecules of hydrocarbons effectively increases the impedance of the membrane, thereby degrading its function as an ion transport medium. In so doing, the energy output of the detector into the fixed input impedance of the amplifier 46 is reduced, the output being inversely proportional to the accumulation of oil. Thus, the decreased signal, as detected at suitable indicator 50, can be translated into a direct reading of oil content of the sample under test. Note that within a short period of operation, effectively all of the oil content of the water sample has been accumulated in the membrane 27, such that a final reading can be taken within a short period of time. Typically, for a sample of about one liter, a final reading can be taken in about one minute.

It is important to note that the action which makes an accurate information-carrying signal available is the fact that the internal impedance of the detector cell decreases roughly directly as a function of the accumulation of oil. By making the input to circuit 46 low compared to the impedance of the device 20, changes in the impedance of device 20 can be accurately detected. Typically the impedance of device 20 before degradation is about 60 ohms, so the input impedance of circuit 46 may be suitably set at about 60 ohms. This can be achieved by connecting leads 45 and 47 across a load resistance of about 60 ohms, and taking the signal from across the resistance and applying it to the input of a DC amplifier. Conventional impedance matching circuits and amplifier circuits, well known in the art, may be utilized to provide an output of any desired strength.

Figure 3:
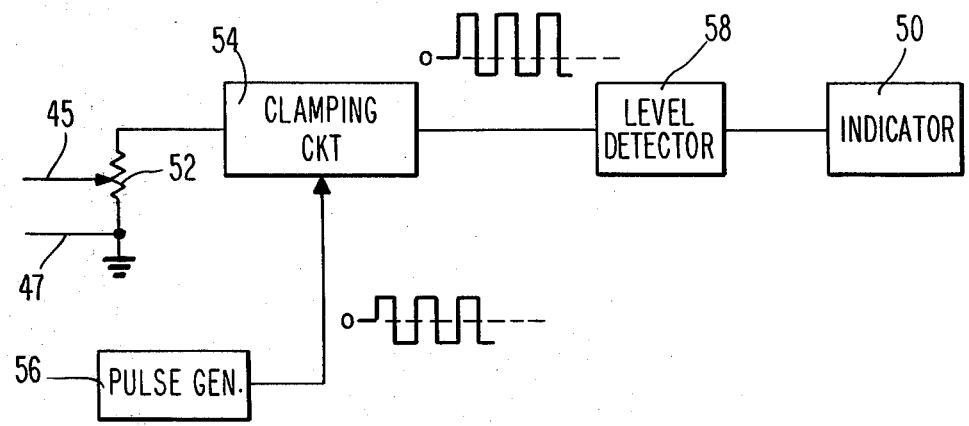
FIG. 3 is a schematic diagram showing another method for electronically generating an indication of the oil content of the water analyzed by the system of this invention.

FIG. 3 represents another form of circuitry for accurately providing a signal representative of the condition of device 20. The leads 45 and 47 are connected to the input wiper of a resistor 52 and to ground respectively, one end of resistor 52 being connected into a clamping circuit 54. Another input terminal of clamping circuit 54 is connected to a standard pulse generator, the clamping circuit acting to produce a pulse output which is clamped at a level which tracks the input signal on lead 45. By this device, the small variations in the large pulse signal, which variations are caused by the change in signal from the detector, can be more accurately detected in a level detector 58, which in turn may contain any desired amount of conventional amplification and processing circuitry. The output of detector 58 is connected to a suitable indicator 50. The output of indicator 50 can be calibrated by simple adjustment of the wiper position of pot 52. The circuitry of FIG. 3 is an embodiment of circuitry adapted to process the low signal to noise ratio output from the device 20.

In operation, the device and system of this invention may be utilized on a boat or in any location where it is desirable to test for the oil content of water. A sample is placed in container 41 and circulated through device 20 by pump 44. Since the detector operates on an accumulation basis, once an oil content in excess of the amount being looked for, e.g., 15 parts per million, has been detected, the detector must either be cleaned or otherwise regenerated or disposed of. The detector may be cleaned by taking the device 20 and washing it thoroughly in detergent and then replacing it in the system. Another technique of regenerating the detector 20 is to fill the sample holder with carbon tetrachloride or any other suitable solvent and circulate it through the detector, thereby washing out the hydrocarbons from the spongy membrane element.

Another procedure for utilization of the oil detection device of this invention is one which may be used with boats having a filter downstream from the bilge pump. The characteristic of the filter is such that as long as it is not filled up, or unsaturated, it passes essentially no hydrocarbons which may be contained in the water coming from the bilge pump, i.e., it is catching all of the hydrocarbons. At the time that it fills up, or saturates, then the oil content of the filter output increases dramatically, since the hydrocarbons are now passing through. In this situation, the detector 20 is placed between the filter output and the discharge over the side of the boat, such that all of the water from the bilge pump is run through the detector. As long as the filter is operable, there is essentially no change in impedance of the detector and no change in the electrical output of the detector due to hydrocarbon buildup. However, when the filter becomes saturated, the reading from the detector output changes substantially abruptly, and thereby gives an indication of the failure of the filter. The indicator for this arrangement suitably provides a simple GO-NO GO reading, which indicates to the user that the filter is either still good or it is not good.

The preferred embodiment of the invention is hydrocarbon sensitive, i.e., it is designed for the analysis of the oil content of water. In other embodiments, other types of organic molecules, which are present in trace amounts, may be tested for. Present regulations which guard against water pollution cover a wide range of industrial effluents, many of which can be analyzed with the detector and system of this invention. The composition of the membrane 27 may be chosen to optimize the detection of different organics, the specific type of spongy material chosen being what is known to be effective in accumulating the specific organic involved in the application.

It is noted that the membrane 27 accumulates the organic molecules, and thus changes its characteristic in response to the integral of the organic molecules in the water being passed through it. This being the case, in applications where the water flow is continuous, it may be desirable to include a differentiating circuit in the signal processing circuit 46 to provide a signal directly representative of the organic content of the water then passing through the detector.

We claim:

1. An oil content analyzing apparatus, comprising:
 a. a housing having openings for water flow therethrough, said water having at least trace amounts of oil therein;
 b. first and second electrode elements positioned within said housing, said elements being of dissimilar metallic composition;
 c. oil absorbing accumulating means positioned between said electrodes for absorbing and accumulating trace amounts of oil from water flowed therethrough; and
 d. output means connected to said electrodes for providing outside of said housing an output signal which is a function of the accumulated oil absorption of said accumulating means.

2. The oil content analyzing apparatus as described in claim 1, wherein said oil absorbing accumulating means is characterized by permitting diffusion of ions therethrough and by absorbing hydrocarbon molecules.

3. The oil content analyzing apparatus as described in claim 2, wherein said oil absorbing accumulating means is composed of polyurethane.

4. The oil content analyzing apparatus as described in claim 3, wherein a first of said electrodes is made of copper and a second of said electrodes is made of zinc.

5. The oil content analyzing apparatus as described in claim 1 further comprising a sample flow means for flowing a sample of water through said housing.

6. The oil content analyzing apparatus as described in claim 5, wherein said sample flow means comprises a sample container, a pump, and fluid connecting means for interconnecting said pump, said container and said housing, whereby said sample of water can be circulated through said housing.

7. The oil content analyzing apparatus as described in claim 6, comprising circuitry for detecting low signal to noise outputs from said output means, and an indicator connected to the output of said low signal to noise circuitry.

8. The oil content analyzing apparatus as described in claim 6, further comprising indicating means connected to said output means for indicating the amount of oil absorbed by said accumulating means.

9. The oil content analyzing apparatus as described in claim 8, wherein said indicator means comprises a low effective load impedance connected across said output means.

10. The oil content analyzing device of claim 1 wherein said oil absorbing accumulating means comprises a spongy material which preferentially absorbs oil in the presence of water.

11. The oil content analyzing apparatus as described in claim 10, wherein said accumulating means is a membrane in close abutting arrangement with a given surface area of each of said two electrodes, each of said electrodes having a coating of porous plastic over at least a portion of the other surfaces thereof.

12. A method of analyzing the oil content of water, the method utilizing a detector having a degradable ion transport membrance sandwiched between two electrodes, comprising the steps of:
 obtaining a sample of said water containing trace amounts of oil therein,
 flowing said sample containing trace amounts of oil through said membrane,
 accumulating oil from said oil in said membrane,
 recirculating said sample through said membrane until substantially all of said trace amounts of oil have been accumulated in said membrane, and
 detecting the electrical output generated across said electrodes, which output varies as a function of said accumulation such that said detected output is a predetermined function of said accumulation.

13. An oil detection device comprising means for accumulating trace amounts of oil in water flowed therethrough, said accumulating means having ion transport characteristics which degrade with the accumulation of oil, said accumulating means being in combination with two electrodes of dissimilar metals, said accumulating means comprising a spongy membrane sandwiched between said electrodes, whereby, when water containing trace amounts of oil is flowed through said oil detection device, said electrodes act as a source with a characteristic which is a function of the oil accumulated by said accumulating means, and further comprising flow means for supplying a flow of water through said device.

14. The oil detection device as described in claim 13, wherein said flow means supplies a recirculated flow of a predetermined amount of said water containing trace amounts of oil.

* * * * *